United States Patent [19]
Ferguson

[11] Patent Number: 5,199,304
[45] Date of Patent: Apr. 6, 1993

[54] APPARATUS FOR OPTICALLY MEASURING SPECIMEN DEFORMATION DURING MATERIAL TESTING

[75] Inventor: Hugo S. Ferguson, Averill Park, N.Y.

[73] Assignee: Duffers Scientific, Inc., Poestenkill, N.Y.

[21] Appl. No.: 839,339

[22] Filed: Feb. 20, 1992

[51] Int. Cl.$^5$ .............................................. G01L 1/024
[52] U.S. Cl. ..................................................... 73/800
[58] Field of Search ...................... 73/800; 356/32, 383, 356/384

[56] References Cited

U.S. PATENT DOCUMENTS

| | | | |
|---|---|---|---|
| 4,129,384 | 12/1978 | Walker et al. | 356/383 |
| 4,836,031 | 6/1989 | Jatho et al. | 73/800 |
| 4,962,669 | 10/1990 | Gernhart et al. | 73/800 |

OTHER PUBLICATIONS

"Electro-optical Position-Measuring System", NASA Tech Briefs, Jan. 1991, p. 26.
Descriptive Advertising Sheet for "Thermecmastor Z" Induction Heated in Thermo-dynamic Material Testing System from Fuji Denpa Koki KK (Japanese).

Primary Examiner—Hezron E. Williams
Assistant Examiner—Nashmiya N. Ashraf
Attorney, Agent, or Firm—Peter L. Michaelson

[57] ABSTRACT

A technique for in a thermo-dynamic material testing system for optically measuring changes in specimen size that occur during material testing. Specifically, a pair of jaws, one movable and one fixed, engage opposite ends of the test specimen and are controllably moved with respect to each other in order to impart a desired tensile or compressive force to the specimen. A fixed light source emits a planar light beam, typically collimated laser radiation, that is directed at the specimen by two mirrors mounted to the jaws and on one side of the specimen. One of these mirrors is secured to and moves with the moving jaw and directs the light beam toward the specimen along a transverse path; the other mirror is mounted to the fixed jaw. A fixed light receiver receives the light beam after it has passed over the specimen and has been reflected by a similar pair of mirrors mounted to the jaws but on the other side of the specimen. Changes in the positional profile of the light beam caused by specimen deformation are detected by the receiver and converted into physical measurements of deformation and deformation rate.

18 Claims, 3 Drawing Sheets

APPARATUS FOR OPTICALLY MEASURING SPECIMEN DEFORMATION DURING MATERIAL TESTING

BACKGROUND OF THE INVENTION

1. Field of the Invention

The invention relates to apparatus for use in a thermo-dynamic material testing system for optically measuring changes in specimen size that occur during material testing.

2. Description of the Prior Art

The materials industry extensively uses a variety of test methods and systems for measuring a wide range of different material characteristics. Since data about the performance and behavior of a particular material must generally be known before that material can be used in practice, material testing methods and systems have become critical to the materials industry. Such data is usually obtained by measuring the performance of a specimen of a particular material under controlled test conditions. For example, the specimen may be subjected to a increasingly large but controlled tensile force in order to determine the specific amount of tensile force that the specimen can withstand without fracturing or the tensile force at which the specimen will break apart. The manner through which the specimen reacts to applied test forces indicates how the underlying material will subsequently perform under actual operating conditions.

Generally speaking, a typical test specimen for use in performing tensile tests comprises a cylindrical length of material with a central portion having a reduced diameter. A longitudinal centrally located portion of this section is considered the gage length (or gage section) of the specimen. In a tensile test, changes in the length and cross-section of the gage length are measured to obtain information about the amount through which the material will "stretch" under load and the amount through which the cross-section of the material will "shrink" to accommodate the "stretch". For diametral measurements during tensile testing to have validity, these measurements are generally made at the center, i.e. the mid-span, of the gage length.

In conventional tensile testing, as the gage length of the specimen changes in size, the mid-span will also translate axially or lengthwise along the specimen. Most tensile testing machines known in the art are equipped with one stationary jaw and one movable jaw, which collectively transmit a tensile force to the specimen. The jaws grip the specimen at each of its ends and are then moved apart at a controlled rate and under a controlled force. Accordingly, as the jaws move apart to place the specimen under tension and thus cause its gage length to elongate, and specifically as the movable jaw travels away from the fixed jaw, the mid-span of the gage length translates along the longitudinal axis of the specimen and in same direction of motion as that of the moving jaw. When the change in length of the specimen is uniform around its gage length, the central portion of the gage length moves in the same direction of motion of the moving jaw but at a rate of travel which is one-half that of the moving jaw.

Machines designed to perform tensile and other similar tests have been in use for many decades. Many of these machines perform tensile tests at relatively slow rates. Traditionally, during such slow-rate testing, mechanical instruments have been used to physically measure the size of the gage length. In particular, to undertake these measurements, such an instrument was usually attached directly to the specimen in the area of the gage length and actually moved with the specimen during the tensile test. In recent years, material testing has also involved compression testing where the specimen is typically reduced in length by application of a controlled compressive force. Slow-rate compressive testing is usually performed with tensile-test type instruments that are attached directly to the specimen in the area of the gage length. In general, these instruments have exhibited adequate performance during such slow-rate testing.

However, during the last few decades, a need has also arisen to measure the mechanical size of the gage length at very high rates of specimen deformation. Unfortunately, mechanical instruments which are merely attached to the specimen gage length in order to measure its length and diameter have generally tended to be quite unreliable when subjected to high physical accelerations. Not surprisingly, in these situations, the instruments produced grossly erroneous readings. This effect stemmed from several causes such as, for example, additional mass and inertia which the instrument itself added to the specimen, difficulties associated with simply keeping the instrument adequately secured to a desired point on the specimen as both the instrument and that portion of specimen collectively moved at relatively high accelerations during high-speed specimen deformation, and the inability of the instrument itself to adequately perform when subjected to high accelerations.

Furthermore, material testing not only occurs at high rates but also at elevated specimen temperatures. In this regard, the temperature of a specimen may be very high during such tests which, in turn, causes additional difficulty in dynamically measuring its physical size while a test is underway. In particular, thermo-dynamic testing systems, particularly the "GLEEBLE" family of systems presently manufactured by the present assignee (which also owns the registered trademark "GLEEBLE"), self-resistively heat a metallic specimen by passing large controlled electrical currents through the specimen during testing in order to significantly raise its temperature. An example of such a system is described in my co-pending United States patent application entitled "A Test Specimen/Jaw Assembly that Exhibits Both Self-Resistive and Self-Inductive Heating in Response to an Alternating Electrical Current Flowing Therethrough", Ser. No. 07/645,190, filed Jan. 18, 1991 which has also been assigned to the present assignee hereof.

Now, to further complicate physical deformation measurement, even when a test specimen is only moderately hot, contacting the specimen with suitable measuring gauges is normally a difficult task at best. However, when the specimen temperature becomes extremely high, e.g. on the order of 3000° C. which can often occur during various tests, the task of physically contacting the specimen to make measurements becomes essentially impossible. Simply stated, such a gauge will itself physically expand and begin to distort, at much lower temperatures, i.e. well before these high temperatures are even reached, thereby totally frustrating the measurements.

Non-intrusive optical measuring techniques have been used widely in many manufacturing, testing and assembly applications to accurately locate the position of an object. In many such systems, changes in the position of an object are often determined by measuring changes in the size or shape of a light beam after that beam has been partially shadowed by the object. The light beam may be formed into a collimated sheet having a width greater than that of the object, or the beam may be a pencil beam that scans one- or two-dimensionally across the object. For example, an optical measuring system that uses laser beams shaped into collimated sheets of light for locating objects in a wind tunnel is described in "Electro-optical Position-Measuring Systems," *NASA Tech Briefs*, January 1991, page 26.

Thus, at first blush, in view of the need for a measurement technique that can function at very high deformation rates and at very high temperatures, optical measurement techniques, which rely on non-contact light based measurements and thus obviate the problems associated with traditional mechanical measurement techniques, would appear to hold great promise when used for measuring specimen deformation in a modern high speed thermo-dynamic material testing system. Accordingly, tensile and compressive testing machines are now frequently equipped with optical specimen measuring systems. However, while optical measurement systems are non-intrusive and yield very accurate results in many diverse applications, the optical measuring systems that to date have been applied to thermo-dynamic material testing systems have exhibited severe drawbacks which have greatly limited their usefulness.

In this regard, various non-intrusive optical techniques are known to measure specimen tensile deformation and deformation rates. Some of these techniques rely on measuring specimen gage length by allowing a light beam to pass through corresponding holes located at each end of the specimen or by illuminating flags that are spaced apart and positioned along the specimen. As noted above, some test specimens are prepared with a reduced mid-span that defines the gage length; this length being the portion situated between two effectively enlarged lateral walls. A light beam can be used to simply scan across the gage length, i.e. where a pinpoint beam itself is oriented in a direction perpendicular to the longitudinal axial direction of gage length but is scanned along and in a direction parallel to the gage length, to detect changes in the spacing between the holes, flags or walls. Alternatively, a collimated light beam shaped as a sheet with a width greater than the gage length can be used, along with a suitable detector, to detect changes in the gage length, as defined by changes in the detected position of shadows cast by the locations of the individual holes, flags or walls as the specimen is being deformed. However, since the beam is scanned over a fixed one- or two-dimensional region of the specimen established prior to its deformation, these techniques fail to account for the axial translation of the mid-span of the gage length as the specimen deforms—thereby yielding inaccurate data.

Accordingly, some optical deformation measuring systems known in the art have tended to use a servo-controlled mirror to steer the light beam during specimen testing. An example of just such a system is the optical measurement system provided by Fuji Denpa Koki KK of Japan on its "THERMECMASTOR Z" induction heated thermo-dynamic testing machine. Other such systems move an optical transmitter or a receiver or both as the specimen changes size. To ensure that, for example, the mid-span is continually measured as it translates during specimen deformation, all of these particular optical measurement systems require tracking systems that, essentially, track the motion of the mid-span of the specimen. These tracking systems then attempt to move the beam in a pre-defined manner such that the beam continues to cross the mid-span as it translates longitudinally along the specimen. Unfortunately, these tracking systems tend to be quite complicated and expensive. Furthermore, and of much greater significance, these tracking systems, which include servo-controlled mechanical actuators to move either the mirror or the transmitter or receiver, generally have overall frequency responses that are often much less than that of the testing machines themselves, i.e. these testing machines can easily and in fact are routinely used to produce deformation rates in the specimen that greatly exceed the maximum rate at which, e.g., the mirror can be accurately positioned. Consequently, with such a tracking system and particularly at very high rates of deformation, the limited frequency response of the optical measurement system can introduce considerable phase lag into the specimen measurements. In fact, in some cases, this lag is so large as to effectively preclude optical measurements from being used at all at very high rates of deformation. In other cases, where such an optical measurement system is used, its response is likely to be simply too slow to follow the rapid translation in the mid-span, thereby producing measurements that simply contain excessive error and are thus of essentially no use.

One optical measurement system known in the art that does not rely on using a servo-controlled positioning system is described in U. S. Pat. No. 4,836,031 (issued Jun. 6, 1989 to Jatho et al and hereinafter referred to as the '031 Jatho et al patent). In particular, this patent describes a technique, which relies on an optical based measurement system, for performing fast-rupture tests on a test specimen. As described therein, separate mirrors are mounted on opposing jaws that grip opposite ends of the specimen and impart a tensile load thereto. A light source emits a collimated light beam that is then reflected by one mirror in a direction oriented along the longitudinal axis of the specimen. The beam travels along the length of the specimen and then strikes the other mirror which, in turn, reflects the beam into a position detector. The detector, which is spaced from the specimen, generates an output signal based upon positional translation (deviation) of the beam. The amount of deformation (denoted as $\Delta s$ in the '031 Jatho et al patent) imparted to the specimen is determined based upon the measured deviation in the beam (there denoted as $\Delta s'$) with simply the deformation rate being the rate of change in the measured deviation.

While the system described in the '031 Jatho et al patent appears to be able to measure an axial change in the length of the specimen, such a measurement is generally not sufficient to fully characterize the deformation which the specimen is undergoing. In this regard, such axial measurements do indicate the length through which the specimen will "stretch" during tensile testing but will not provide any indication of any change in the "shrinkage" of the cross-section of the specimen as it is being deformed in tension, let alone at the translating mid-span where such measurements should in fact be taken.

Thus, a need exists in the art for an optical based measurement technique, particularly one suited for use in a thermo-dynamic material testing system, for accurately and rapidly measuring changes in the cross-section of the translating mid-span of the specimen while the specimen is being deformed at a very high rate and at a very high temperature.

SUMMARY OF THE INVENTION

In accordance with the teachings of my invention, I have advantageously solved the deficiencies associated with using optical measurement systems known in the art in a high speed thermo-dynamic material testing systems for measuring specimen deformation as well as deformation rate.

My invention contains an optical system that controllably moves a light beam to accurately track the mid-span and measure, for example, its diameter (or width), as the mid-span of the specimen translates and changes in size during specimen deformation.

Specifically, my inventive apparatus utilizes an optical measurement system in conjunction with a pair of jaws that engage opposite ends of a test specimen. A hydraulic power source, such as a piston rod from an appropriate hydraulic cylinder, moves one of the jaws to stretch or compress the specimen. The measurement system utilizes a fixed light source to emit a light beam that is directed at the specimen by two beam deflectors, preferably mirrors (or prisms or the like) mounted on a common side of both jaws. A first one of these mirrors, to which the output of the light source is directed, is secured to the fixed jaw; while a second one of these mirrors, which receives light reflected off the first mirror, is secured to the movable jaw. The mirrors, particularly the second mirror, is initially positioned such that the light beam incident from the first mirror will be reflected from the second mirror and travel along a plane that perpendicularly bisects the gage section (i.e. at the mid-span) of the specimen prior to the start of its deformation. The same double mirrored arrangement exists on the opposite side of the specimen. The light beam is scanned along a bounded one-dimensional distance, so as to produce a planar scanning beam, which is sufficiently large to include the complete cross-section of the mid-span, even after, for example, expansion due to a compressive deformation. A detector receives the scanning light beam after it has transversed the mid-span and has been reflected by the pair of mirrors mounted on this latter side of the jaws. Changes in the shape and location of the detected light beam, particularly shadows therein, caused by deformations, either compressive or tensile, are detected to determine the amount and rate of specimen deformation.

In operation, the mirror(s) are first adjusted, prior to the start of specimen deformation, such that the beam transverses the gage section along its mid-span, i.e. along a plane that bisects the gage section. Then, during the ensuing deformation, as the corresponding mirrors move in unison with the movable jaw, the reflected beam will horizontally translate at half the speed and distance through which this jaw moves. Furthermore, the mid-span of the gage section will itself also translate at half the speed and distance through which this jaw moves and in a longitudinal axial direction along the specimen. Consequently, the reflected scanning beam that transverses the specimen will substantially, if not exactly, track and remain coincident with the mid-span as it axially translates along the specimen during the entire deformation. By maintaining the beam in transverse alignment with the translating mid-span, an accurate real-time cross-sectional measurement of the gage section of the specimen can be made as the specimen simultaneously undergoes compressive or tensile deformation.

Furthermore, my inventive measuring system can readily and continuously measure the length of the gage section during specimen deformation. To achieve this, the orientation of the planar scanning beam is changed, for example by rotating the light source by 90°, such that the scanning beam, as it traverses the specimen, is oriented parallel rather than perpendicular to the longitudinal axis of the specimen. Through movement of the mirror(s), the beam will axially translate along the specimen as the gage section lengthens during tensile deformation. If a sufficiently wide beam is used to encompass a maximum expected elongation in the gage section, then this entire section will remain continuously illuminated by the beam as this section is deformed.

Advantageously, since my inventive apparatus only requires that the mirrors be fixedly secured to the jaws and simply relies on the movable jaws to position the appropriate mirrors without any of the mirrors being separately positionable (i.e. without the use of any servo-controlled tracking systems) or requiring any other moving parts, the response of my inventive optical measuring apparatus easily matches that of the thermo-dynamic material testing system to which it is attached. As such, this permits my inventive measurement apparatus to yield real-time deformation measurements that can also be used for dynamic control of the testing system.

Furthermore, a feature of my inventive measurement apparatus readily permits the measuring beam to be set to translate longitudinally along the specimen at nearly any ratio of the movement of the mid-span of the gage section. To provide this, the angular orientations of the first and second mirrors is simply adjusted such that the light beam, emanating from the light source and reflected off the first mirror, strikes the second mirror at an appropriate angle. This angle is set such that light reflected from the second mirror remains perpendicular to the axis of the specimen and initially strikes the gage section at a point located along the gage section but at a distance, as measured from an end of the section, equal to the desired ratio of the total length of the gage section.

To conveniently locate the optical transmitter and receiver in suitable locations, additional mirrors may be used to direct both an incoming light beam produced by the light source and an outgoing light beam from the specimen. However, the only mirror required to move the beam at one-half (or other ratio) of the rate and distance through which the mid-span of the gage section translates during deformation is the particular mirror, attached to the movable jaw, onto which the light beam impinges before it is reflected onto the specimen.

BRIEF DESCRIPTION OF THE DRAWINGS

The teachings of my invention will be readily understood by considering the following detailed description in conjunction with the accompanying drawings, in which.

To facilitate understanding, identical reference numerals have been used, where possible, to identify identical elements that are common to various figures.

DETAILED DESCRIPTION

After reading the following description, those skilled in the art will certainly realize that the broad teachings of my inventive optical measuring system can be used to accurately and dynamically measure deformation in a wide variety of different material testing systems that rely on relative movement of two jaws to grip opposing ends of a test specimen and, through relative movement thereof, impart a deformatory force to the specimen. Nevertheless, for purposes of illustration and to simplify the following discussion, I will specifically discuss my invention for use in conjunction with a "GLEEBLE" testing system, such as the GLEEBLE 2000 system, manufactured by Duffers Scientific of Poestenkill, N.Y. (which is also the current assignee hereof and also owns the registered trademark "GLEEBLE"). Furthermore, only those portions of this system that are specifically relevant to the present invention will be discussed herein. For a more detailed discussion of this system, the reader is referred to my co-pending United States patent applications: "A Test Specimen/Jaw Assembly that Exhibits Both Self-Resistive and Self-Inductive Heating in Response to an Alternating Electrical Current Flowing Therethrough", Ser. No. 07/645,190, filed Jan. 18, 1991; and "A Dynamic Thermal-Mechanical Material Testing System Utilizing a Balanced Field" Ser. No. 07/694,911 filed May 2, 1991 (both of which have also been assigned to the present assignee hereof).

Figure 1:
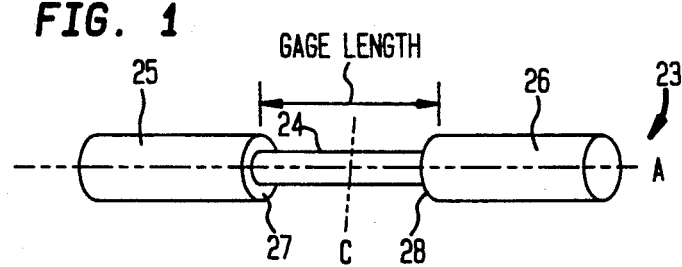
FIG. 1 depicts a pictorial view of a typical and conventional tensile specimen.

FIG. 1 shows typical and conventional tensile specimen 23 that is tested in a GLEEBLE 2000 thermo-dynamic material testing system. This specimen, while particularly adapted for length measurements of the gage section, is non-standard for tensile measurements. In this regard, the enlarged end portions tend to corrupt the strain that will occur at each end of the gage length.

As shown, specimen 23, having longitudinal axis A, is formed of a cylindrical length of material with central portion 24 having a reduced diameter. With this configuration, the specimen has raised (enlarged) end portions 25 and 26, with corresponding lateral walls 27 and 28. The reduced central portion is defined to be the gage length (or gage section). For a tensile test, changes in the length of the gage section and cross-section of the mid-span (the mid-span labeled "C") of the gage length, i.e. the latter being taken across a plane that traverses the mid-span and is perpendicularly oriented to longitudinal axis A, are measured to obtain information about the amount through which the material will "stretch" under load and the amount through which the cross-section of the material will "shrink" to accommodate the "stretch". Generally speaking, the gage length is typically 2" in length (approximately 5 cm) for a type "505" specimen (i.e. a cylindrical specimen of 0.505 inches (approximately 1.28 cm) in diameter). The gage length is generally chosen to be 4 times the diameter of the specimen and centrally located along the longitudinal axis of the specimen. In some testing applications, particularly in Europe, relatively small gage lengths, such as on the order of 20-30 mm, are used instead. While specimen 23 is shown as having a round cross-section, my inventive measuring technique will also accurately measure specimens having other cross-sectional shapes, such as square or rectangular. Specifically, excellent results accrue from my technique with specimens shaped in the form of bars or sheets of appropriate sizes.

Figure 2:
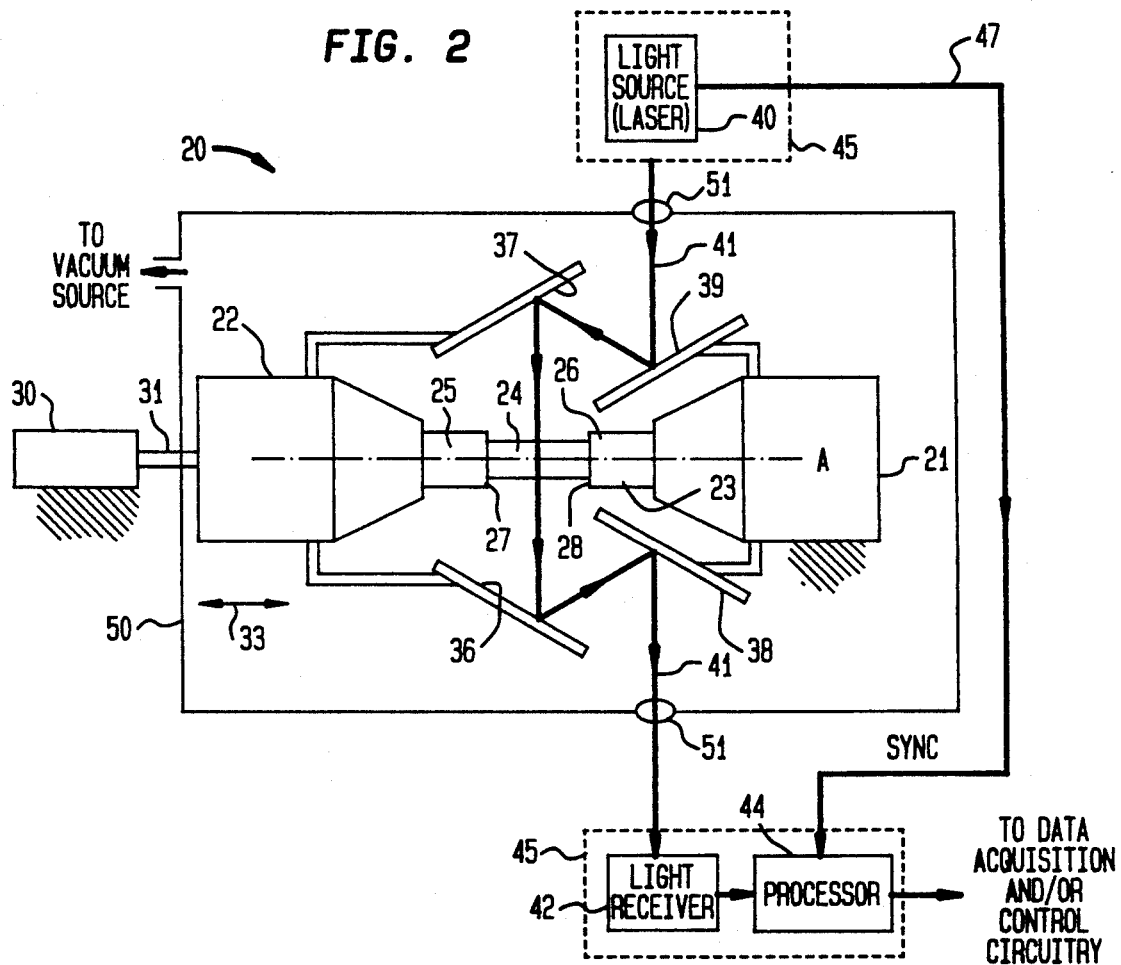
FIG. 2 depicts a simplified view of a tensile/compressive test stand which contains a preferred embodiment of my inventive optical measuring system.

FIG. 2 depicts a simplified diagrammatic view of a salient portion of a tensile/compressive test stand which contains a preferred embodiment of my inventive optical measuring system. As shown, test stand 20 has stationary jaw 21 and movable jaw 22. Test specimen 23 is conventionally supported between both of these jaws. Jaw 22 is connected, via piston rod 31, to hydraulic cylinder 30. Under suitable and well-known servo-hydraulic control, this cylinder appropriately positions jaw 22 over a pre-defined distance, and with controlled velocity, to impart an appropriate tensile or compressive force to specimen 23 and oriented, in the direction shown by double arrow 33, along the longitudinal axis of the specimen. When jaw 22 is moved towards jaw 21, specimen 23 is subjected to a compressive force. Contrarily, when jaw 22 is moved away from jaw 21, specimen 23 is subjected to a tensile force.

Figure 3:
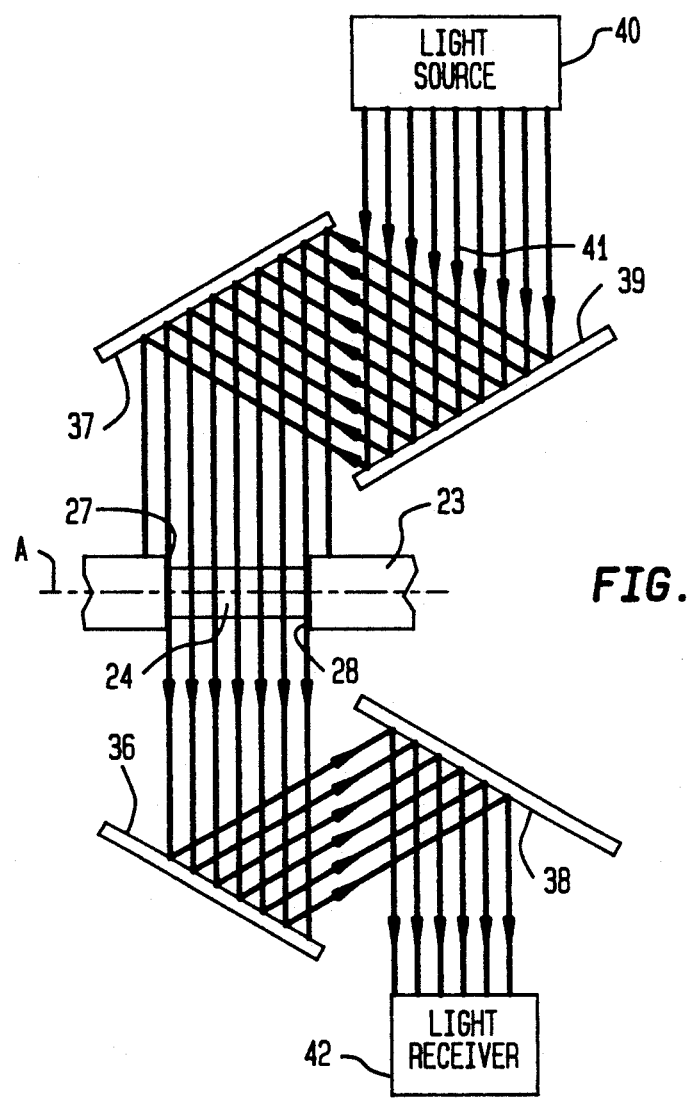
FIG. 3 depicts a simplified diagrammatic view showing illustrative transmission paths for the scanned light beam for measuring the length of the specimen gage section using my inventive optical measuring system.
Figure 4:
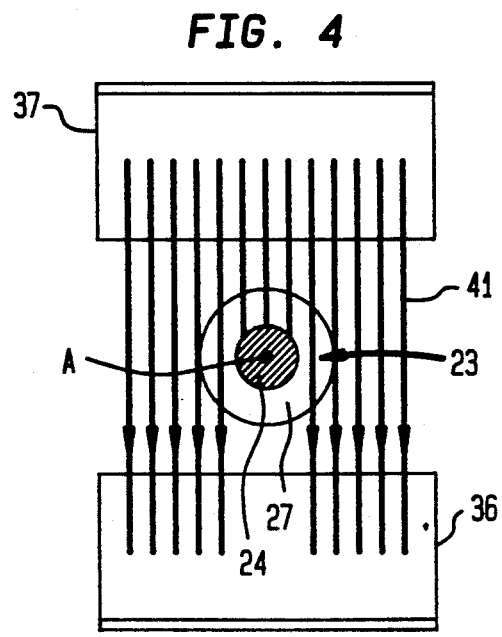
FIG. 4 depicts a simplified diagrammatic view, taken in a direction perpendicular to the viewing direction of FIG. 2 and along the longitudinal axis (A) of the specimen, showing illustrative transmission paths for the cross-scanned light beam for measuring the cross-section of the mid-span using my inventive optical measuring system.

A pair of planar mirrors 36 and 37 is fixed to movable jaw 22 and positioned on opposite sides of the specimen. A second pair of planar mirrors 38 and 39 is fixed to stationary jaw 21 with their reflecting surfaces positioned in the optical path of mirrors 36 and 37. Light source 40, which is preferably a one- or two-dimensional scanning laser, is positioned to direct light beam 41 at mirror 39. Although the light beam is shown as a single ray in this FIG. 2, in actuality, this beam is formed of a ray that is scanned over a finite distance, in effect forming collimated thin sheet that extends in a single plane over this distance. To measure the diameter of the specimen cross-section (or width in the case of a rectangular or square shaped cross-section) of the mid-span, the planar beam is oriented to traverse the mid-span of the specimen and in a direction perpendicular to longitudinal axis A, as shown in FIG. 4. With respect to FIG. 2, beam 41 would scan over a finite distance that extends in a plane normal to the plane of the figure. Alternatively, to measure changes in length of the gage section, beam 41 would be oriented, as shown in FIG. 3 and as discussed below, to scan along the specimen gage length and in a direction parallel to its longitudinal axis.

Although a variety of laser transmitters that can produce such a scanning beam is readily available in the commercial marketplace, we have obtained excellent results through use of a Model 1102 Laser Dimension System manufactured by Zygo Corporation of Middlefield, Conn. This system, represented by dashed boxes 45, contains light source 40, light receiver 42 and associated processor 44. This system utilizes approximately a 1 mW output He-Ne laser which emits light at 632.8 nm over a 2 inch (approximately 5 cm) wide scanning beam. With such a system, light source 40 utilizes a single laser and a rotating mirror. During system operation, the mirror continuously rotates to direct the light emitted from the laser, in a raster fashion, across a scanning width. Receiver 42 contains a spherical lens which focuses beam 41 onto a single photodetector. In order to synchronize the processor 44 to produce a positional profile that accurately coincides with the position of the scanning beam, source 40 routes a synchronization (sync) signal, via line 47, to processor 44 at the start of each raster scan. Clearly, any one of a wide variety of other commercially available laser based positioning systems can also be used.

Owing to very narrow bandwidth, collimated and coherent wave characteristics of laser emitters, a laser should preferably be used as light source 40. In particular, whenever specimen 23 is glowing, it is emitting light across a rather wide spectrum of both visible and infra-red wavelengths. However, relatively little power is radiated at any one such wavelength. Accordingly, the narrow bandwidth of the laser radiation combined with the use of an appropriate radiation filter on receiver 42 and tuned to the wavelength of the laser can substantially reduce any interference attributable to radiation emitted from the specimen which might otherwise corrupt the optical measurements by receiver 42. This, in turn, advantageously increases an overall signal-to-noise ratio associated with the measuring system.

The light receiver is positioned to receive reflections of light beam 41 after it has traversed the specimen and has been reflected by mirrors 36 and 38. This receiver merely detects a raster-based positional profile of beam 41. The resulting profile, in turn, is applied, to processor 44, which converts changes in the profile specifically caused by movement of shadows in a detected planar light pattern into values, based upon the particular orientation of the measuring beam, into a desired physical measurement, such as mid-span cross-sectional diameter (or width) or length of the gage section. This conversion occurs by selecting an appropriate pair of leading and trailing edges in the detected positional profile, measuring the relative distance therebetween and, through an appropriate formula or proportionality constant, transforming the measured distance into the desired physical dimension. The resulting dimensional values, in turn, are applied from processor 44 to associated well-known data acquisition systems (such as recorders and the like, all of which is not shown) or, as a feed back signal, through appropriate well known electronic circuits and servo-hydraulic systems (all not shown), to control the operation of cylinder 30 based upon actual specimen deformation. Through use of an appropriate proportionality factor or formula, a value of the cross-sectional area of the mid-span could be obtained from the mid-span diameter measurement— though the resulting area value would contain some degree of error if the mid-span cross-sectional shape ceased to remain circular during testing. Inasmuch as laser dimension system 45 is well-known in the art, its specific operation will not be discussed any further herein.

The relative positions of mirrors 36–39 with respect to light source 40, receiver 42 and specimen 23 are all properly adjusted before deformation begins. Mirror 39 directs incoming (incident) light produced by light source 40 towards mirror 37 which, in turn, reflects this light, as an "entering" beam, towards the specimen. The resulting light in beam 41 that is not blocked by the specimen, i.e. an "exiting" beam, is reflected from mirror 36 and directed to mirror 38. This latter mirror directs the resulting light in beam 41 to light receiver 42.

Specifically, with the light source and receivers in the positions shown, mirror 39 is adjusted at an angle of 30° with respect to the longitudinal axis of specimen 23 with its reflecting surface facing away from the specimen. Mirror 37 is oriented such that a 60° angle exists between the incident and reflected rays of beam 41 that, for this mirror, will be directed towards specimen 23 and perpendicular to its longitudinal axis. Mirrors 36 and 38 are similarly adjusted. With this orientation, beam 41 will track and remain coincident with the mid-span of the gage section as that mid-span translates along the longitudinal axis. In this regard, the beam will translate at the same velocity and across the same distance as will the mid-span; namely one-half of the speed and through one-half of the distance through which jaw 22 moves. Once the orientation of all these mirrors is manually set each of these mirrors is locked into position through suitable set screws or the like (not shown). After being so locked, jaw 22 and mirrors 36 and 37 all move together as a single unit. Clearly, these mirrors can be appropriately adjusted to different angles, as discussed below, such that beam 41 will traverse the specimen at a different point and will translate across the specimen at nearly any ratio of the movement of the mid-span of the gage section.

The positions of mirrors 38 and 39, as well as their angular orientation, can also be appropriately changed in order to accommodate placing light source 40 and receiver 42 in convenient locations. Should such changes occur, the angular orientation of mirrors 36 and 37 may also have to be changed accordingly in order to direct beam 41 to traverse specimen 23 along its mid-span and provide a 60° angle between the incident and reflected rays for mirrors 36 and 37. Furthermore, mirrors 38 and 39 can be deleted entirely with appropriate re-location of light source 40 and receiver 42. In addition, depending upon the location of receiver 42, mirror 36 need not have a similar angular orientation as mirror 37.

All of these mirrors are preferably so-called "laser mirrors" and can be obtained from illustratively Oriel Corporation of Stratford, Conn. The mirrors are appropriately sized, based on the size of the specimen, to prevent becoming overlapped by the position of the jaws prior to the start of tensile deformation. For relatively short specimens, such as with gage lengths under 2 inches (approximately 5 cm), mirrors 38 and 39 can each be 1 inch (approximately 2.5 cm) in diameter with mirrors 36 and 37 each being 2 inches (approximately 5 cm) in diameter. For longer specimens, mirrors 38 and 39 can each be 2 inches in diameter (approximately 5 cm); mirrors 36 and 37 can each be 4 inches (approximately 10.2 cm) in diameter. Appropriate mirrors are Oriel model numbers 44270, 44190, and 44150 for the 4, 2 and 1 inch diameter sizes. However, owing to a potential for these round mirrors to physically overlap the light beam emanating from light source 40, rectangularly shaped mirrors can alternatively be used for all these mirrors in order to permit increased travel distances for moving mirrors 36 and 37 without blocking this beam.

In order to provide good reflectivity for the low power output (1 mW) of the He-Ne laser within laser dimension system 45, each of these mirrors utilizes front surface reflection. Furthermore, to prevent the surface of the mirrors from oxidizing at elevated specimen temperatures, each of these mirrors should have an appropriate protective anti-oxidant coating on its reflective surface. Illustratively, for an aluminum base mirror, such as those specified above, a manganese fluoride coating with a thickness of ¼ wavelength (3,164 Angstroms for 632.8 nm radiation) yields excellent results.

In addition, elevated temperature material testing is frequently performed under vacuum conditions. As such, the jaws, specimen and mirrors are contained within vacuum chamber 50 which is connected to a well-known vacuum source (not shown) that evacuates the chamber to a desired pressure level. Accordingly, housing 50 contains crown glass windows 51 which are positioned within the optical path to permit beam 41 to properly enter and exit the housing. Each of these windows also has an appropriate anti-oxidant protective coating and can also be obtained from the Oriel Corporation. All of the optical components should be selected in accordance with well established laser techniques known in the art.

To measure changes in the length of gage section 24, beam 41 is oriented, as shown in FIG. 3, in a scanning direction parallel to longitudinal axis A. This can be readily accomplished by rotating light source 40 to change the orientation of beam by 90°. With this new orientation, beam 41 must have a total scanned width that is greater than the maximum gage length to be achieved during the test. In addition, mirror 37 must direct beam 41 toward specimen 23 such that beam 41 intercepts walls 27 and 28 throughout the entire test, particularly in view of the full axial translation of the beam. Alternatively, as shown in FIG. 4, beam 41 can be oriented in a scanning direction perpendicular to longitudinal axis A in order to measure the diameter (or width) of the mid-span of the specimen. As the width of the mid-span changes, it will intercept more or less of the collimated rays of beam 41.

Figure 5:
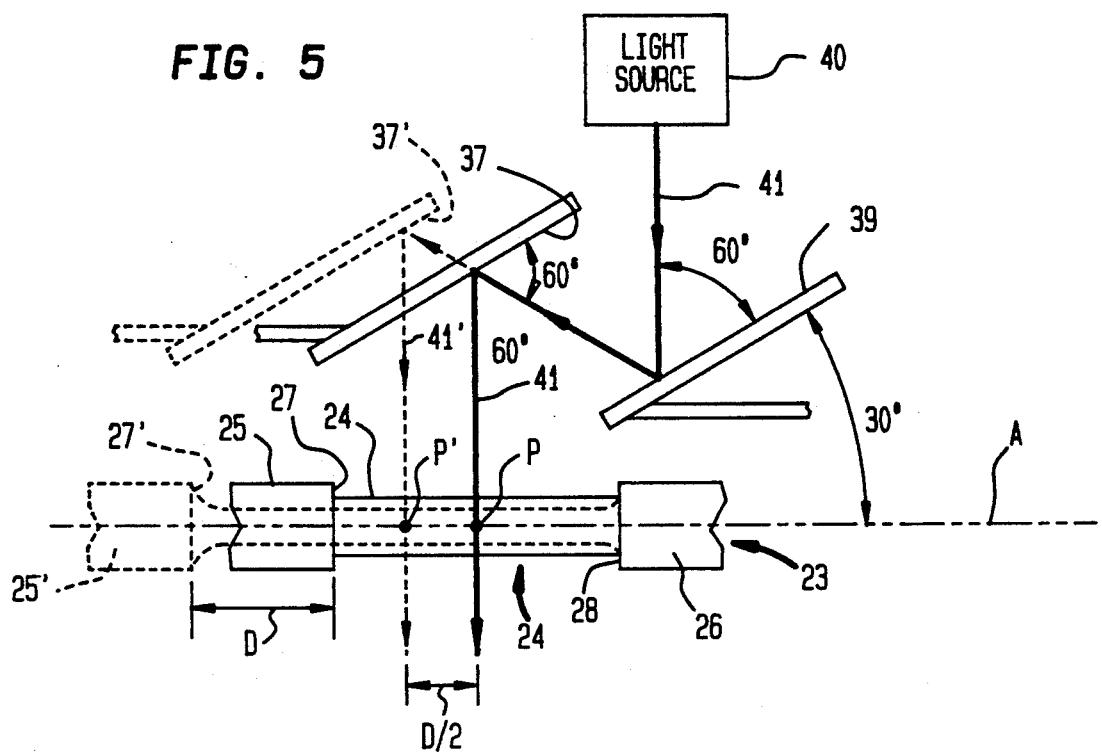
FIG. 5 depicts a simplified diagrammatic view of a portion of the preferred embodiment illustrating its operation for the most common orientation of the mirrors.

As discussed above, for a desired measurement, scanning beam 41 must properly translate longitudinally across specimen 23 with respect to movement of the mid-span of the specimen. Different angular settings for the mirrors will determine the rate at which the scanning beam will translate with movement of the movable jaw. FIG. 5 illustrates operation of my inventive measuring system for the most common orientation of the mirrors, i.e. that which, as discussed above, maintains beam 41 over the translating mid-span of the specimen. Specifically, given the angular orientation described above, i.e. mirror 39 being oriented at a 30° with respect to longitudinal axis A and with an angle of 60° for mirror 37 between incident and reflecting portions of beam 41 associated therewith, central point P, i.e. the midspan, will move at one-half the rate of increase (tensile test) or decrease (compressive test) of the gage length. As specimen 23 is pulled in tension through a distance D by movement of raised end portion 25, the cross-section of the specimen will shrink, as indicated by a dotted line profile, the mid-span originally located at point P will translate, through distance D/2, to new position P' and beam 41 will precisely follow. Mirror 37 will also translate through distance D. To clarify the drawing, end section 25, wall 27 and mirror 37, after moving a distance D, are designated as 25' and 27' and 37', respectively.

Figure 6:
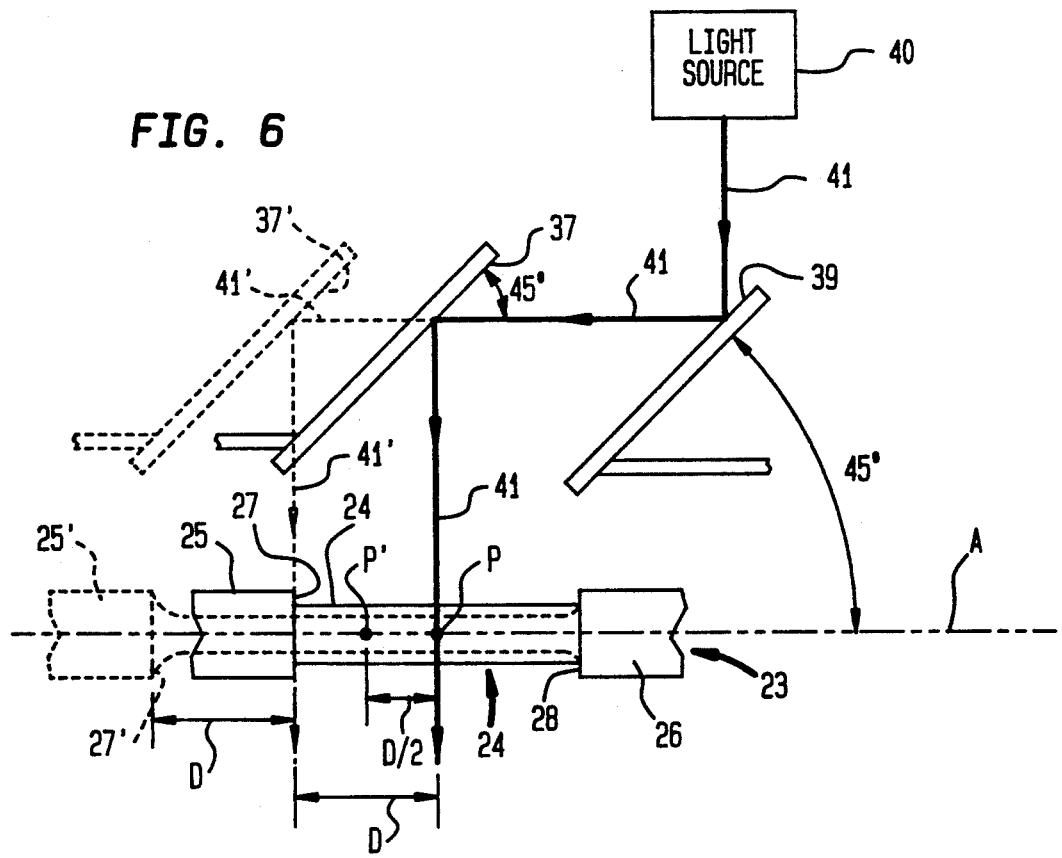
FIG. 6 depicts a simplified diagrammatic view, similar to the view of FIG. 5, showing a portion of the preferred embodiment and illustrating its operation for another orientation of the mirrors.

FIG. 6 depicts a simplified diagrammatic view, similar to the view of FIG. 5, showing a portion of the preferred embodiment and illustrating its operation for another orientation of the mirrors. Here, mirrors 37 and 39 are oriented at 45° angles (as opposed to 30°) with respect to longitudinal axis A. Mirror 39 directs beam 41 at mirror 37 along a 45° line to insure that beam 41 passes specimen 23 in a perpendicular direction to its axis A. As the gage length increases by distance D, beam 41 also axially translates through distance D. By virtue of translating through this distance, beam 41 no longer coincides with the new mid-span location, i.e. central point P'. As such and owing to the 45° degree orientation of the mirrors, beam 41 has moved at a rate that is twice the rate of center point P. Of course, numerous other mirror orientations are possible. The rate of beam movement, depending upon the specific mirror orientation chosen, may be set to a value that is greater or less than the rate of movement of the specimen midspan.

While I have thusfar described my invention in terms of use with cylindrical specimens having a reduced gage length, my inventive optical measuring system will function with many other forms of specimens. In this regard, the gage length may be also be defined with holes located at either end of the specimen rather than with a reduced central diametric portion. The portion of the specimen lying between the holes defines the gage length. However, specimens, with a non-uniform cross-sectional area either resulting from the presence of holes or even with enlarged shoulders, are frequently problematic. In this regard, the presence of holes in either end of a specimen or the increased diameter of end portions 25 and 26 of specimen 23 often causes significant non-uniform material strength near the ends of the gage section. In addition, whenever the specimen is self-resistively heated (through heating currents and associated electrical equipment all of which is not shown), the specimen must have a uniform resistance in order to exhibit uniform heating particularly with isothermal planes throughout. Inasmuch as non-uniform cross-sectional areas produces resistive non-uniformities near the end sections, these non-uniformities yield locally non-uniform heating. This corrupts the isothermal nature of a resulting heat profile in the specimen and, in certain tests, effectively rules out the use of a specimen with non-uniform cross-sectional area. To use my inventive optical measuring system in these situations, special markers may be placed on a specimen of uniform cross-section in order to define the gage length.

Figure 7:
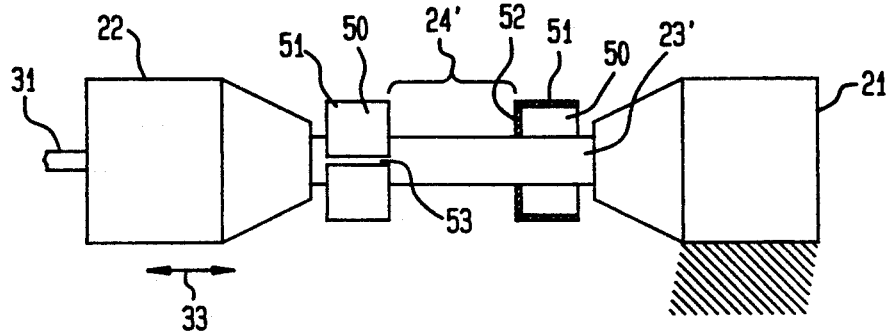
FIG. 7 a side elevation, partly in section, of a specimen of uniform cross-section with opaque light shields that can be used in conjunction with my inventive optical measuring system.

Specifically, FIG. 7 depicts a side elevation, partly in section, of a specimen of uniform cross-section with opaque light shields (optical markers) that can be used in conjunction with my inventive optical measuring system. As shown, cylindrical specimen 23' of uniform cross-section is mounted in jaws 21 and 22 in the same manner described above with respect to specimen 23. Cylindrical specimen 23' may be of any uniform cross-sectional shape such as circular or rectangular. An identical light shield 50 is mounted at either end of specimen 23' to define gage length section 24'. The light shields may be made of a low-cost, single use material, such as carbon. Alternatively, the light shields can be made of a sturdier material, such as a suitable ceramic, and used on a repetitive basis inasmuch as the shields will simply slip off the specimen after it has cooled.

Each of shields 50, one of which is shown in cross-section, includes cylindrical sleeve 51 with a ring-shaped end wall 52. This wall has an opening substantially congruent to the cross-sectional shape of 35 specimen 23'. Each of shields 50 has a slot 53 to accommodate thermal expansion and frictional mounting on specimen 23'. Each of these shields is preferably of a material with very low thermal conductivity, such as ceramic or carbon, for use in thermal tests where the temperature of the specimen is to be substantially raised. Furthermore, the light shields are each preferably thin and light weight so as to be easily held in place by frictional forces that occur between the surfaces of specimen 23' and wall 52. The thermal coefficient of expansion of light shields 50 is preferably chosen to be smaller than that of specimen such that as the specimen temperature is elevated, the specimen expands into increasingly tighter abutment with the shields. Alternatively, each of these shields can be made of an appropriately resilient material (and without the use of slots 53) that can withstand high temperatures.

The wall thickness of walls 52 is preferably small (though not critical) so that shields 50 contact specimen 23' only over a very short length thereby defining the gage length more precisely and without appreciably affecting the specimen response to the applied stress.

Furthermore, similar light shields can be used with a specimen, rather than having a uniform cross-section throughout its entire length as is the case with specimen 23', that has a gage length that is uniform in cross-section and then smoothly transitions at either end thereof from the gage length cross-section to the cross-section of an adjacent raised end portion. With such a specimen, a light shield can be affixed in the vicinity of each end of the gage section. However, rather than being a ring with a single-slotted cylindrical extension and adapted to "slip over" each end of the specimen as in the case of shields 50, the light shield would have an internal joint to permit the shield to be opened and, once appropriately positioned onto the gage section, to be closed and, in turn, secure the shield in position. Depending upon the material used to construct the shield, it may still utilize a slot to accommodate anticipated thermal expansion of the shield and/or the specimen.

Although I have described my invention as employing only one measuring beam oriented either parallel or perpendicular to the longitudinal axis of the specimen, those skilled in the art will readily appreciate that two such beams oriented in an orthogonal fashion can be simultaneously used to measure mid-span cross-section and length of the gage section in parallel. This, of course, generally necessitates the use of duplicated laser positioning systems in which the laser source and receiver in each system is appropriately oriented to measure a corresponding physical dimension. Alternatively, a single scanning light beam can be used in lieu of two scanning beams provided that single beam were to be scanned, such as on a raster basis, over a two-dimensional area to encompass both mid-span cross-section and the maximum expected length of the gage section.

Furthermore, other suitably reflective optical elements, such as prisms, may be substituted for each of the mirrors. If a single frequency laser is used within light source 40, then a simple prism can be used in place of any of the mirrors.

Although a single embodiment which incorporates the teachings of my present invention has been shown and described in detail herein, those skilled in the art can readily devise many other varied embodiments that still incorporate these teachings.

I claim:

1. Apparatus for a material testing system for imparting controlled deformation to a test specimen and for simultaneously measuring a physical dimension associated therewith, said apparatus comprising:
   first and second opposing jaws for holding opposing ends of a test specimen, said specimen having a longitudinal axis, said first jaw being movable and said second jaw being fixed, wherein said first jaw is controllably positioned with respect to the second jaw so as to produce a pre-defined force in said specimen and oriented along said longitudinal axis thereby causing a controlled amount of compressive or tensile deformation to occur in said specimen;
   means for producing a collimated planar beam of radiation with a pre-defined orientation, said producing means being fixed in position;
   first light reflecting means, secured to said first jaw at a first side thereof and oriented at a first pre-defined angle with respect to said longitudinal axis, for reflecting said beam incident thereat in a planar orientation towards said specimen, as an entering beam, so as to traverse a pre-defined portion of said specimen to be measured;
   second reflecting means, secured to said first jaw at a second side opposite to said first side and oriented at a second pre-defined angle with respect to said longitudinal axis, for reflecting portions of said beam not blocked by said specimen, as an exiting beam;
   a beam detector, being fixed in position and responsive to said exiting beam, for producing a detected signal; and
   means, responsive to said detected signal, for converting said detected signal into a pre-defined physical dimension for said specimen.

2. The apparatus in claim 1 wherein the orientation of said planar beam and first pre-defined angle are selected such that said entering beam reflected from said first light reflecting means is oriented in a direction substantially perpendicular to the longitudinal axis of said specimen so as to traverse said specimen at a pre-defined point along said longitudinal axis, and wherein said pre-defined first angle is selected such that said point translates axially across said specimen at a predefined ratio of distance through which said first jaw moves as said specimen is controllably deformed.

3. The apparatus in claim 2 wherein said first angle is set to thirty degrees such that said entering beam will traverse and remain substantially coincident with a mid-span of said specimen as said mid-span axially translates during specimen deformation.

4. The apparatus in claim 3 wherein said physical dimension is mid-span diameter or mid-span width.

5. The apparatus in claim 4 wherein said beam is a light beam.

6. The apparatus in claim 5 wherein said light beam is a planar collimated scanning laser beam having a pre-defined scanning width.

7. The apparatus in claim 6 wherein said detected signal is a positional profile of said beam.

8. The apparatus in claim 7 further comprising:

a third and fourth reflecting means, attached to opposing sides of said second jaw for reflecting said collimated planar beam emanating from said beam producing means towards said first reflecting means and for reflecting said exiting beam reflected from said second reflecting means towards said beam detector, respectively; and third and fourth reflecting means being oriented at third and fourth pre-defined angles with respect to said longitudinal axis;

wherein said third pre-defined angle is selected to orient said collimated planar beam to said first reflecting means from said beam producing means such that said beam will traverse said specimen in said planar perpendicular orientation, and said second and fourth pre-defined angles are selected so as to direct said exiting beam to said beam detector.

9. The apparatus in claim 8 wherein said first and third reflecting means are co-located along a common first side of said specimen, and said second and fourth reflecting means are co-located along a second common side of the specimen opposite from the first common side thereof.

10. The apparatus in claim 9 wherein said first, second, third or fourth reflecting means is a laser mirror or prism.

11. The apparatus in claim 1 wherein the orientation of said planar beam and first pre-defined angle are selected such that said entering beam reflected from said first light reflecting means is oriented in a direction substantially parallel to the longitudinal axis of said specimen so as to traverse said specimen throughout a pre-defined gage section thereon centrally located between said opposing ends, and wherein said pre-defined first angle is selected such that said planar beam traverses the entire gage section as said specimen is deformed.

12. The apparatus in claim 11 wherein said physical dimension is length of the gage section.

13. The apparatus in claim 12 wherein said beam is a light beam.

14. The apparatus in claim 13 wherein said light beam is a planar collimated scanning laser beam having a pre-defined scanning width.

15. The apparatus in claim 14 wherein said detected signal is a positional profile of said beam.

16. The apparatus in claim 15 further comprising:

third and fourth reflecting means, attached to opposing sides of said second jaw for reflecting said collimated planar beam emanating from said beam producing means towards said first reflecting means and for reflecting said exiting beam reflected from said second reflecting means towards said beam detector, respectively; said third and fourth reflecting means being oriented at third and fourth pre-defined angles with respect to said longitudinal axis;

wherein said third pre-defined angle is selected to orient said collimated planar beam to said first reflecting means from said beam producing means such that said beam will traverse said specimen in said planar perpendicular orientation, and said second and fourth pre-defined angles are selected so as to direct said exiting beam to said beam detector.

17. The apparatus in claim 16 wherein said first and third reflecting means are co-located along a common first side of said specimen, and said second and fourth reflecting means are co-located along a second common side of the specimen opposite from the first common side thereof.

18. The apparatus in claim 17 wherein said first, second, third or fourth reflecting means is a laser mirror or prism.

* * * * *